(12) United States Patent
Say et al.

(10) Patent No.: US 6,464,849 B1
(45) Date of Patent: Oct. 15, 2002

(54) SENSOR FOR MEASURING A BIOANALYTE SUCH AS LACTATE

(75) Inventors: James L. Say, Alameda; Henning Sakslund, Pleasant Hill; Michael F. Tomasco, Danville, all of CA (US)

(73) Assignee: Pepex Biomedical, L.L.C., Ada, MI (US)

( * ) Notice: Subject to any disclaimer, the term of this patent is extended or adjusted under 35 U.S.C. 154(b) by 0 days.

(21) Appl. No.: 09/414,060

(22) Filed: Oct. 7, 1999

(51) Int. Cl.[7] ............................................... G01N 27/26
(52) U.S. Cl. ........................ 204/403.14; 204/403.15; 204/403.01
(58) Field of Search ............................ 204/403, 416, 204/403.01, 403.14, 403.15

(56) References Cited

U.S. PATENT DOCUMENTS

| | | |
|---|---|---|
| 4,008,717 A | 2/1977 | Kowarski |
| 4,573,968 A | 3/1986 | Parker |
| 4,640,821 A | 2/1987 | Mody et al. |
| 4,734,184 A | 3/1988 | Burleigh et al. |
| 4,919,649 A | 4/1990 | Timothy et al. |
| 5,004,583 A | 4/1991 | Guruswamy et al. |
| 5,112,455 A * | 5/1992 | Cozzette et al. ............ 205/778 |
| 5,165,406 A | 11/1992 | Wong |
| 5,220,920 A | 6/1993 | Gharib |
| 5,243,982 A | 9/1993 | Möstl et al. |
| 5,264,105 A | 11/1993 | Gregg et al. |
| 5,271,815 A | 12/1993 | Wong |
| 5,330,634 A | 7/1994 | Wong et al. |
| D354,347 S | 1/1995 | Knute et al. |
| D354,559 S | 1/1995 | Knute et al. |
| 5,384,028 A | 1/1995 | Ito |
| 5,431,174 A | 7/1995 | Knute |
| 5,503,728 A * | 4/1996 | Kaneko et al. ............ 204/403 |
| 5,505,828 A | 4/1996 | Wong et al. |
| 5,512,159 A | 4/1996 | Yoshioka et al. |
| 5,609,749 A | 3/1997 | Yamauchi et al. |

FOREIGN PATENT DOCUMENTS

| | | |
|---|---|---|
| EP | 0 256 415 A2 | 2/1988 |
| EP | 0 327 658 A1 | 8/1989 |
| EP | 0 420 296 A1 | 4/1991 |
| WO | WO 96/22730 | 8/1996 |

OTHER PUBLICATIONS

Jaraba et al. ("NADH amperometirc sensor based on poly93–methylthiopene)–coated cylindrical carbon fiber microelectrodes: application to the enzymatic determination of L–lactate", Electrochimica Acta, vol. 43, No. 23, pp. 3555–3565, 1998).*

Netchiporouk et al. ("Properties of carbon fibre microelectrodes as a basis for enzyme biosensors", Analytica chimica Acta 303 (1995) 275–283).*

Sakslund, H. et al., "Development and evaluation of glucose microsensors based on electrochemical codeposition of ruthenium and glucose oxidase onto carbon fiber microelectrodes," *Journal of Electroanalytical Chemistry*, vol. 397, pp. 149–155 (1995).

Sakslund, H. et al., "Analysis of the factors determining the sensitivity of a miniaturized glucose biosensor made by codeposition of palladium and glucose oxidase onto an 8 µm carbon fiber," *Journal of Electroanalytical Chemistry*, vol. 402, pp. 149–160 (1996).

* cited by examiner

*Primary Examiner*—Jill Warden
*Assistant Examiner*—Alex Noguerola
(74) *Attorney, Agent, or Firm*—Merchant & Gould P.C.

(57) ABSTRACT

The present disclosure relates to a sensor including a bundle of electrically conductive fibers. The sensor also includes a sensing material coating at least some of the fibers in the bundle, and an insulating layer that surrounds the bundle of electrically conductive fibers.

15 Claims, 6 Drawing Sheets

SENSOR FOR MEASURING A BIOANALYTE SUCH AS LACTATE

FIELD OF THE INVENTION

This invention relates to sensors for measuring bioanalytes and to methods for making such sensors. More particularly, the invention relates to sensors for sensing lactate and to methods for making such sensors.

BACKGROUND OF THE INVENTION

Lactate is a small molecule that is produced by all tissues and organs of a patient's body that are in "distress." Wherever in the patient's body the demands for oxygen exceed the supply, then a state of low perfusion exists and lactate is produced. For example, lactate is produced if a patient is bleeding, if a patient's heart is failing, if a person's limb is in danger of being lost, or if a person is not getting enough oxygen to breathe. Thus many life and limb threatening clinical states produce elevated blood lactate levels, even in the face of adequate oxygen delivery to the patient. It is a matter of oxygen supply and metabolic demand.

At the cellular level, lactate is inversely proportional to the vital cellular energy stores of adenosine triphosphate and is produced within six seconds of inadequate perfusion or cellular injury. It is thus an ideal biochemical monitor of cellular viability at the tissue level, and of patient viability at the systemic level.

Clinically, the dire significance of elevated and rising blood lactate values is known. Trauma physicians and clinical evidence support the hypothesis that a simple, inexpensive, continuous, monitor of lactate in the trauma setting, will save lives by providing timely, life-saving information that will help dictate triage and therapy. For example, an emergency room patient who has a blood lactate level of 4 mM has a 92% mortality rate within the next 24 hours. If this level is 6 mM, then the mortality rate rises to 98%. In animal experiments, blood lactate levels begin to rise within minutes of hemorrhage, and conversely, begin to fall just as quickly with adequate resuscitation. In multivariate analysis, blood lactate is the best indicator of the degree of shock (superior to blood pressure, heart rate, urine output, base deficit, blood gas and Swan-Ganz data) and is proportional to the shed blood volume. Blood lactate levels correlate with a trauma patient's chances of survival. Therapy that fails to control a patient's increasing lactate levels must be modified or additional diagnoses quickly sought.

Sensors have been developed for detecting lactate concentrations in a given fluid sample. For example, U.S. Pat. Nos. 5,264,105; 5,356,786; 5,262,035; and 5,320,725 disclose wired enzyme sensors for detecting analytes such as lactate or glucose.

SUMMARY OF THE INVENTION

One aspect of the present invention relates to a sensor including a bundle of electrically conductive fibers. The sensor also includes a sensing material coating at least some of the fibers in the bundle, and an insulating layer surrounding the bundle of electrically conductive fibers. The conductive fibers provide a large substrate surface area for supporting the sensing material. Thus, the sensor has a large surface area of sensing material even at small sizes. This large surface area of sensing material provides numerous advantages. For example, the large surface area assists in improving the response/sensing time of the sensor. Also, the large surface area assists in lengthening the useful life of the sensor.

Another aspect of the present invention relates to a method for making a sensor. The method includes applying a sensing material to a bundle of electrically conductive fibers. The method also includes covering the bundle of electrically covered fibers with an insulating layer after the sensing material has been applied to the fibers.

These and various other features which characterize the invention are pointed out with particularity in the attached claims. For a better understanding of the invention, it's advantages, and objectives obtained by its use, reference should be made to the drawings and to the accompanying description, in which there is illustrated and described preferred aspects of the present invention.

BRIEF DESCRIPTION OF THE DRAWINGS

The accompanying drawings, which are incorporated in and constitute a part of this specification, illustrate several aspects of the invention and together with the description, serve to explain the principles of the invention. A brief description of the drawings is as follows.

DETAILED DESCRIPTION

Reference will now be made in detail to exemplary aspects of the present invention which are illustrated in the accompanying drawings. Wherever possible, the same reference numbers will be used throughout the drawings to refer to the same or like parts.

An aspect of the present invention relates to sensors for providing on-line monitoring/measurement of bioanalytes in a patient. One particular aspect of the present invention relates to a sensor for providing on-line measurement of lactate concentrations in a patient.

Figure 1:
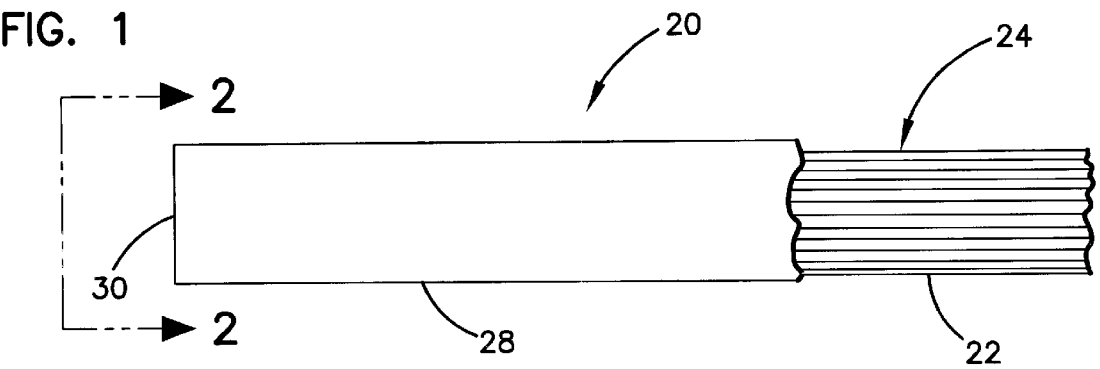
FIG. 1 is an elevational view of a sensor constructed in accordance with the principles of the present invention.
Figure 2:
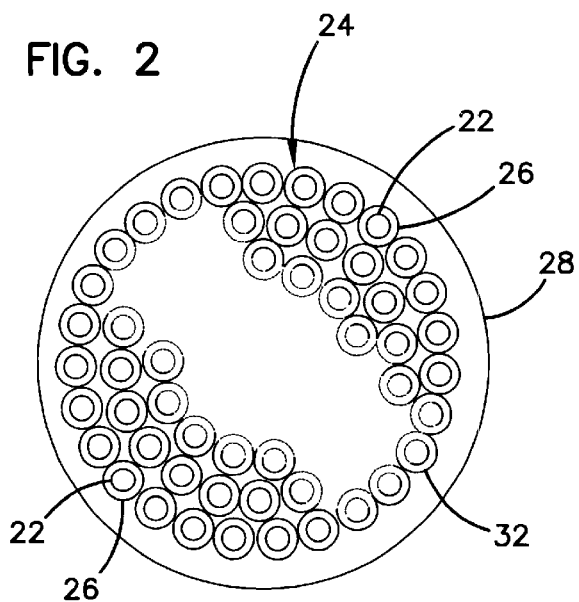
FIG. 2 is a cross-sectional view taken along section line 2—2 of FIG. 1 with only a portion of the fiber ends depicted.
Figure 3:
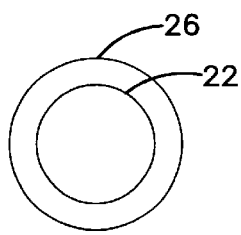
FIG. 3 is a detailed end view of one of the fibers of the sensor of FIG. 1, the fiber is coated with a sensing material.

FIGS. 1–3 illustrate a sensor 20 constructed in accordance with the principles of the present invention. The sensor 20 includes a plurality of electrically conductive fibers 22 arranged in a bundle 24. The fibers 22 in the bundle 24 are coated (i.e. covered) with a sensing material 26. An insulating layer 28 surrounds the bundle 24.

The fibers 22 of the sensor 20 are made of an electrically conductive material. A preferred material of the fibers 22 is carbon. For example, in one nonlimiting embodiment of the present invention, the fibers 22 are made of 92–98% carbon. The fibers 22 will each typically have a relatively small diameter. For example, in one particular nonlimiting environment, the fibers 22 can each have a diameter in the range of 5–10 microns. It will be appreciated that the illustrated embodiments are not drawn to scale. While any number of fibers 22 could be used to form the bundle 24, it is preferred for many fibers (e.g., 1,000 to 3,000 fibers per bundle) to be used. Preferably, the bundle 24 has a diameter in the range of 0.010–0.015 inches.

The sensing material 26 preferably includes a redox compound or mediator. The term redox compound is used herein to mean a compound that can be oxidized or reduced. Exemplary redox compounds include transition metal complexes with organic ligands. Preferred redox compounds/mediators are osmium transition metal complexes with one or more ligands having a nitrogen containing heterocycle such as 2,2'-bipyridine. The sensing material can also include a redox enzyme. A redox enzyme is an enzyme that catalyzes an oxidation or reduction of an analyte. For example, a glucose oxidize or glucose dehydrogenase can be used when the analyte is glucose. Also, a lactate oxidize or lactate dehydrogenase fills this role when the analyte is lactate. In systems such as the one being described, these enzymes catalyze the Pelectrolysis of an analyte by transferring electrons between the analyte and the electrode via the redox compound.

The insulating layer 28 of the sensor 20 preferably serves numerous functions to the sensor 20. For example, the insulating layer 28 preferably electrically insulates the fibers 22. Additionally, the insulating layer 28 preferably provides mechanical strength for maintaining the fibers 22 in the bundle 24. Additionally, the insulating layer 28 preferably forms a barrier about the fibers 22 that prevents the uncontrolled transport of a substance desired to be sensed (e.g., an analyte such as glucose or lactate). In one nonlimiting embodiment, the insulating layer 28 is made of a polymeric material such as polyurethane.

The insulating layer 28 preferably defines an opening for allowing a substance desired to be sensed to be transported or otherwise conveyed to the sensing material 26. For example, the sensor 20 can include a distal end 30 that is transversely cut. At the distal end 30, the insulating layer 28 defines an opening 32 (shown in FIG. 2) through which the material desired to be sensed can be transported. For example, the opening 32 is configured to allow an analyte such as lactate or glucose to diffuse into the sensing material 26 that surrounds the fibers 22.

Figure 4:
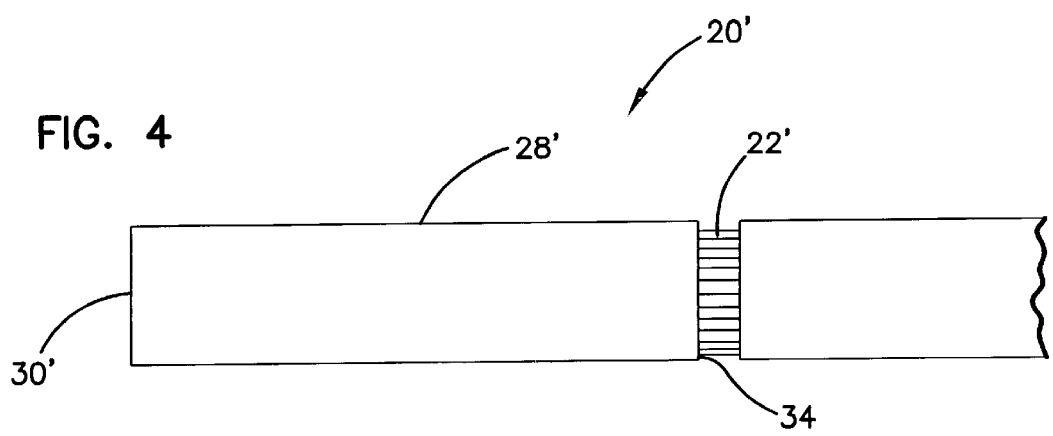
FIG. 4 is a elevational view of an alternative sensor constructed in accordance with the principles of the present invention.

It will be appreciated that openings can be formed at various locations along the length of the sensor 20. For example, FIG. 4 illustrates an alternative sensor 20' having an opening 34 formed at an intermediate location along the length of the sensor 20'. The opening 34 is arranged in the form of an annular cut form through an insulating layer 28' of the sensor 20'. Fibers 22' coated with sensing material are located within the insulating layer 28'. The opening 34 exposes a region of the sensing material to the exterior of the sensor 20'. Consequently, the opening 34 provides a passage for allowing a substance desired to be sensed to diffuse into the region of exposed sensing material. The sensor 20' preferably also includes a distal end 30' that is closed or otherwise sealed by the insulating layer 28'.

Figure 5:
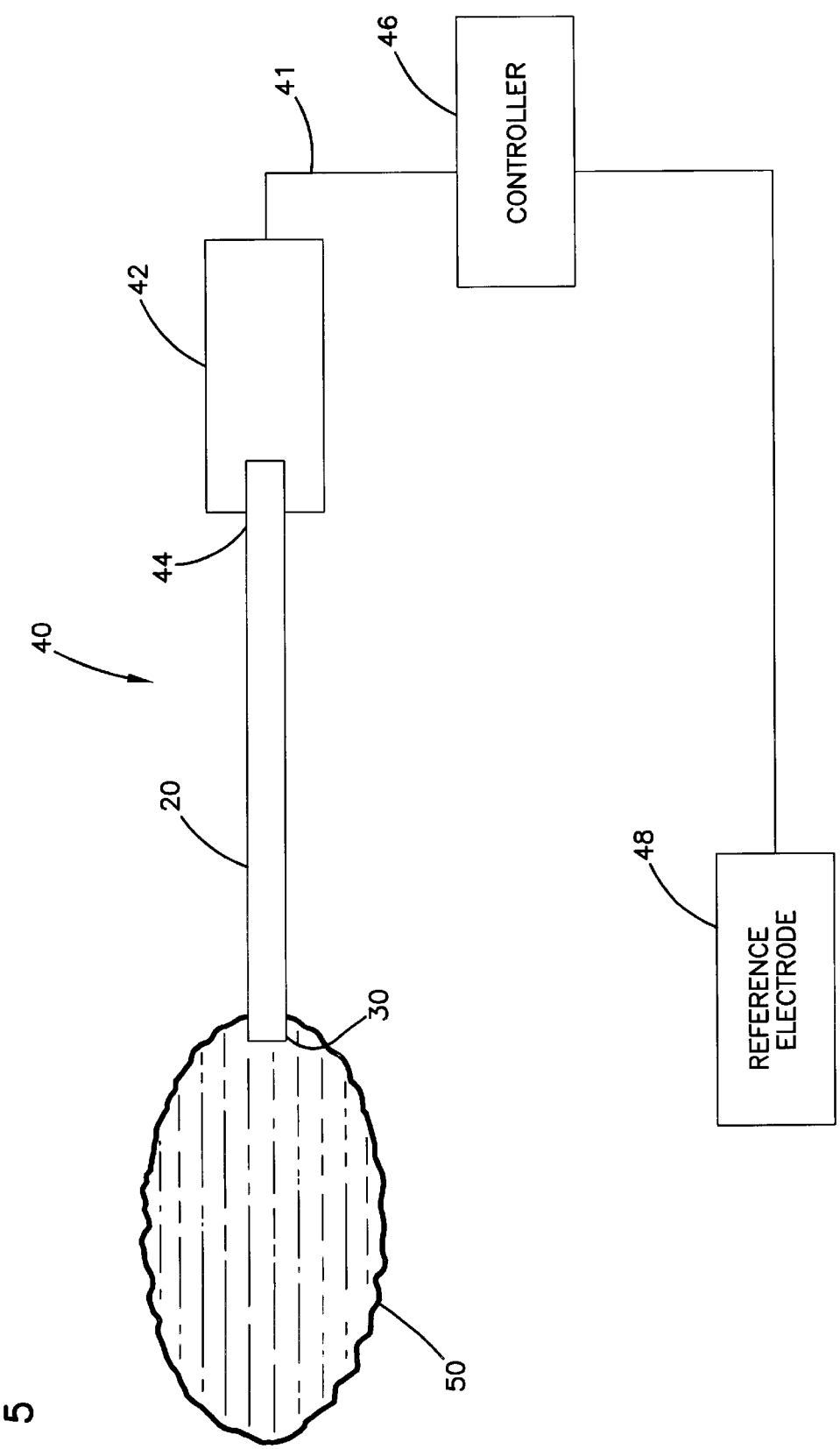
FIG. 5 is a schematic view of a sensor system incorporating the sensor of FIG. 1.

FIG. 5 illustrates a sensing system 40 that incorporates the sensor 20 of FIGS. 1–3. The fibers 22 are electrically connected to a wire 41 by one or more electrical connectors 42 positioned at a proximal end 44 of the sensor 20. The wire 41 electrically connects the sensor 20 to a controller 46. The controller 46 can be any type of controller such as a micro-controller, a mechanical controller, a software driven controller, a hardware driven controller, a firmware driven controller, etc. The controller 46 is also electrically connected to a reference electrode 48. The reference electrode 48 preferably includes a layer of silver silver-chloride.

In use of the sensing system 40, the distal end 30 of the sensor 20 is placed in fluid communication with a test volume 50 of a substance containing an analyte desired to be sensed. The test volume 50 is the volume from which the analyte desired to be sensed can diffuse into the sensor 20 during the sensing period. With the sensor 20 so positioned, the analyte within the test volume 50 can diffuse into the sensing material 26 located adjacent to the distal end 30 of the sensor 20. Additionally, water within the test volume 50 can diffuse into the sensing material 26 such that the sensing material 26 is hydrated. A potential is then applied between the reference electrode 48 and the sensor 20. When the potential is applied, an electrical current will flow through the test volume 50 between the reference electrode 48 and the distal end 30 of the sensor 20. The current is a result of the electrolysis of the analyte in the test volume 50. This electrochemical reaction occurs via the redox compound in the sensing material 26 and the optional redox enzyme in the sensing material 26. By measuring the current flow generated at a given potential, the concentration of a given analyte in the test sample can be determined. Those skilled in the art will recognize that current measurements can be obtained by a variety of techniques including, among other things, coulometric, potentiometric, amperometric, voltammetric, and other electrochemical techniques.

Figure 6A:
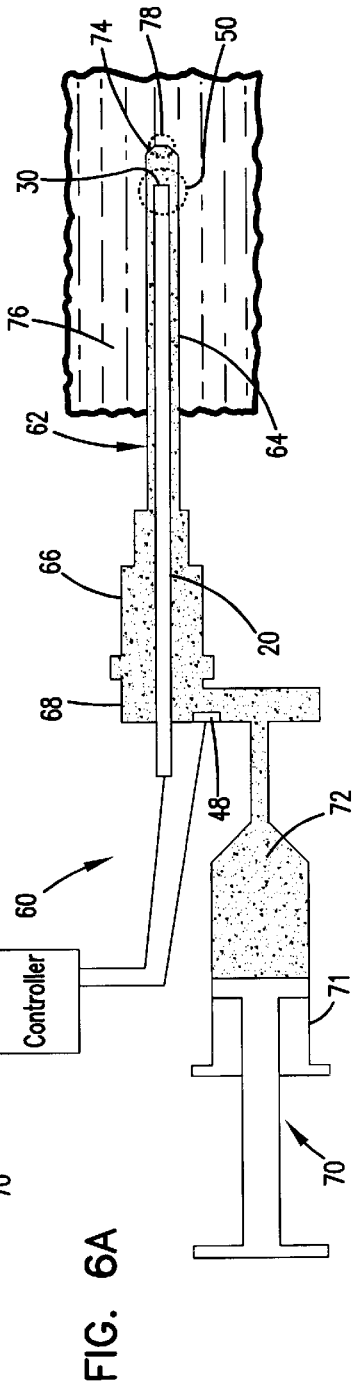
FIG. 6A is a schematic view of a sensor assembly constructed in accordance with the principles of the present invention, the sensor assembly is shown in a start or calibration condition.
Figure 6B:
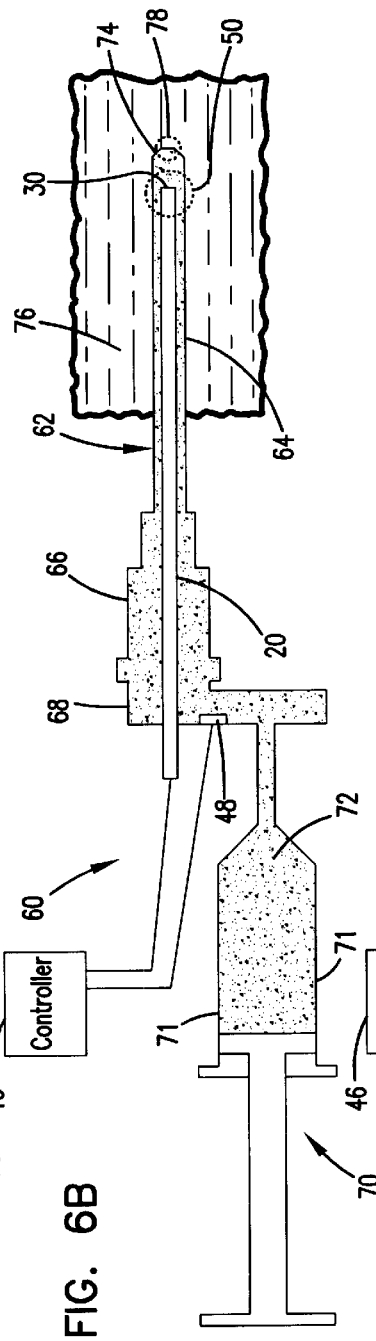
FIG. 6B illustrates the sensor assembly of FIG. 6A in a test condition.
Figure 6C:
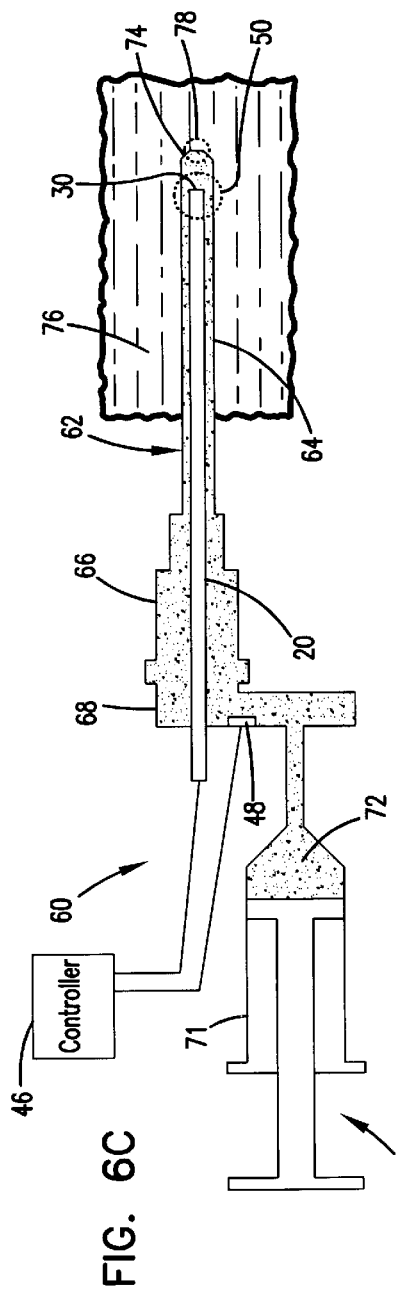
FIG. 6C illustrates the sensor assembly of FIG. 6A in a purge condition.

FIGS. 6A–6C schematically illustrate a sensor assembly 60 for providing on-line monitoring/measurement of bio-analytes such as lactate in a patient. The sensor assembly 60 includes a catheter 62 (e.g., a peripheral catheter) having a catheter sheath 64 connected to a catheter hub 66 (i.e., a luer fitting). The sensor assembly 60 also includes an adapter 68 connected to the catheter hub 66. The adapter is in fluid communication with a pump 70 (e.g., a syringe 71 driven by a syringe driver (not shown)). The syringe 71 preferably contains a volume of calibration fluid 72.

The sensor assembly 60 of FIG. 5 is preferably incorporated into the sensor assembly 60. For example, as shown in FIGS. 6A–6C, the sensor 20 extends through the adapter 68 and into the catheter sheath 64 such that the distal end 30 of the sensor 20 is located adjacent a tip 74 of the catheter sheath 64. In certain embodiments, a radial spacing of at least 0.0015 inches exists between the outer surface of the sensor 20 and the inner surface of the sheath 64. Also, the reference electrode 48 is shown positioned within the adapter 68 and both the reference electrode 48 and the sensor 20 are shown electrically connected to the controller 46.

As indicated above, the syringe 71 preferably contains a calibration fluid 72. The calibration fluid 72 preferably includes a predetermined concentration of a calibrant such as lactate or lactate sensors or glucose for glucose sensors. The calibration fluid can include a variety of other components in addition to a calibrant. For example, an anticoagulant such as sodium citrate can be used. A preferred calibration fluid comprises a solution of sodium citrate, saline, and lactate. Of course, lactate is only used as a calibrate if a lactate sensor is being used in the system. Other types of calibrates that may be used in the system include glucose, potassium, sodium, calcium, and ringers lactate.

FIG. 6A illustrates the sensor assembly 60 at a start condition. As shown in FIG. 6A, the catheter sheath 64 is inserted within a patient such that blood 76 surrounds the tip 74 of the catheter sheath 64. At the start condition, the catheter sheath 64 is filled with the calibration fluid 72 such that the distal tip 30 of the sensor 20 is bathed in the calibration fluid 72. It will be appreciated that with the catheter sheath 64 inserted within the patient, a diffusion zone 78 exists adjacent the catheter sheath tip 74. The diffusion zone 78 is the region into which blood can readily diffuse or mix even when the system is static.

Still referring to FIG. 6A, the test volume 50 of the sensing system 40 surrounds the distal end 30 of the sensor 20. The test volume 50 includes the volume surrounding the distal end 30 of the sensor 20 that is readily depleted of a test substance (e.g., lactate or glucose) when potential is applied between the sensor 20 and the reference electrode 48. It is preferred for the test volume 50 to not be coextensive with the diffusion zone 78. To achieve this, it is preferred for the distal end 30 of the sensor 20 to be located at least one-half millimeter away from the tip 74 of the catheter sheath 64. In certain embodiments, the distal end 30 of the sensor 20 is located in the range of 2 to 3 millimeters away from the catheter sheath tip 74.

While the reference electrode 48 is shown positioned within the adapter 68, it will be appreciated that other configurations could also be used. For example, the reference electrode 48 could comprise a skin mounted electrode positioned on the patient's skin adjacent to the catheter sheath 64. Furthermore, as shown herein, only two electrodes (i.e., the reference electrode 48 and the sensor 20) are used in the sensor assembly 60. It will be appreciated that in alternative embodiments, three electrodes (e.g., a reference electrode, a counter electrode, and a worker electrode) can be used. Exemplary wired enzyme sensors having three electrode configurations are described in U.S. Pat. Nos. 5,264,105; 5,356,786; 5,262,035; and 5,320,725, which are hereby incorporated by reference.

Referring again to FIG. 6A, with the distal end 30 of the sensor 20 bathed in the calibration fluid, a potential can be applied between the reference electrode 48 and the sensor 20. When the potential is applied between the sensor 20 and the reference electrode 48, the sensing material 26 begins to consume the sensed analyte (i.e., the analyte desired to be sensed or measured such as lactate or glucose) within the calibration fluid located in the test volume 50. Initial calibration can be obtained by monitoring the slope of decay in the current generated between the sensor 20 and the reference electrode 48. A reading is preferably taken when the sensor 20 begins to consume all of the analyte in the test volume 50 and the current begins to decline.

After the sensor 20 has been calibrated, a blood sample can be tested. For example, as shown in FIG. 6B, to test a blood sample, the syringe plunger is drawn back such that blood 76 is drawn into the catheter sheath 64. Preferably, sufficient blood 76 is drawn into the catheter sheath 64 to surround the distal end 30 of the sensor 20 with blood and to ensure that the test volume 50 is filled with blood. Once sufficient blood has been drawn into the catheter sheath 64, movement of the plunger is stopped and a potential is applied between the sensor 20 and the reference electrode 48. With the potential applied between the reference electrode 48 and the sensor 20, the sensor 20 begins to consume the sensed analyte contained within the blood 76 within the test volume 50. When the sensor 20 approaches consuming all of the analyte within the test volume 50, the current begins to decline and a reading is taken.

Thereafter, the system is purged as shown in FIG. 6C by pushing the plunger of the syringe 71 inward causing the calibration fluid to displace the blood 76 within the sheath 64. Consequently, the blood 76 within the sheath 64 is forced back into the patient. Preferably, the syringe 71 injects enough of the calibration fluid 72 into the system to displace about two times the volume of the catheter sheath 64. As a result, some of the calibration fluid is injected into the patient along with the blood 76.

After the system has been purged, the sensor 20 can be recalibrated as described with respect to FIG. 6A. Thereafter, the testing and purging steps can be repeated.

The sensor 20 provides numerous advantages. For example, the plurality of fibers 22 provide a large surface area for supporting the sensing material 26. Therefore, a large surface area of sensing material 26 is exposed to the test volume 50. As a result, the sensor 20 is capable of quickly depleting the sensed analyte within the test volume 50 thereby allowing an analyte concentration to be quickly determined. This rapid sensing capability is particularly advantageous for applications such as fetal monitors and intercranial monitors. The large surface area also prevents the sensing material 26 from quickly becoming depleted thereby lengthening the useful life of the sensor 20. Furthermore, the use of carbon fibers assists in accurately calibrating the sensor 20 because carbon is an effective heat conductor. This is significant because some calibration processes are temperature dependent. By using a heat conductive fiber, the temperature of the fiber will quickly match the temperature of a calibration fluid contained within the test volume 50. As a result, calibration inaccuracies associated with differences in temperature between the calibration fluid and the sensor 20 can be reduced.

Figure 7:
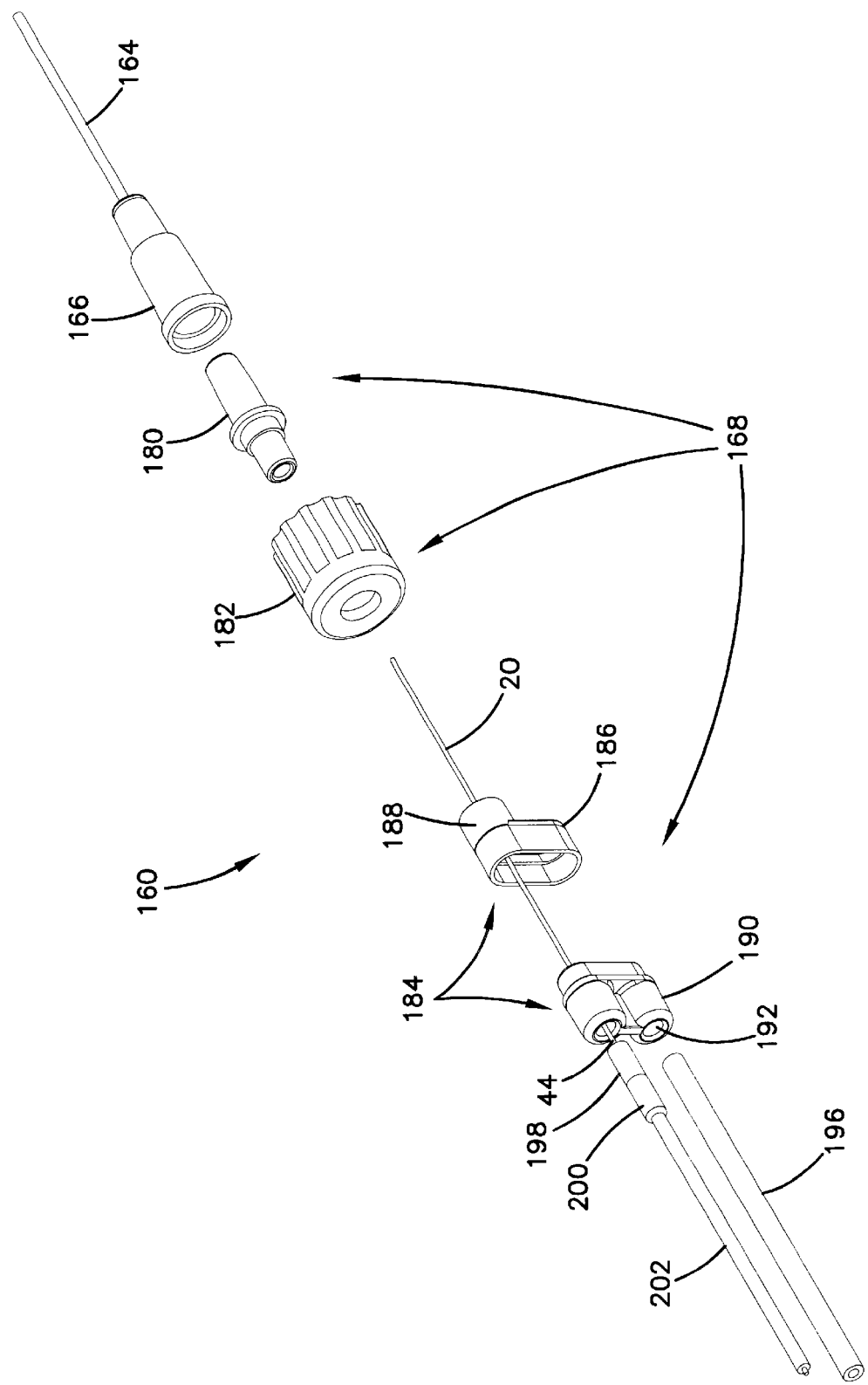
FIG. 7 is an exploded, perspective view of an alternative sensor assembly constructed in accordance with the principles of the present invention.
Figure 8:
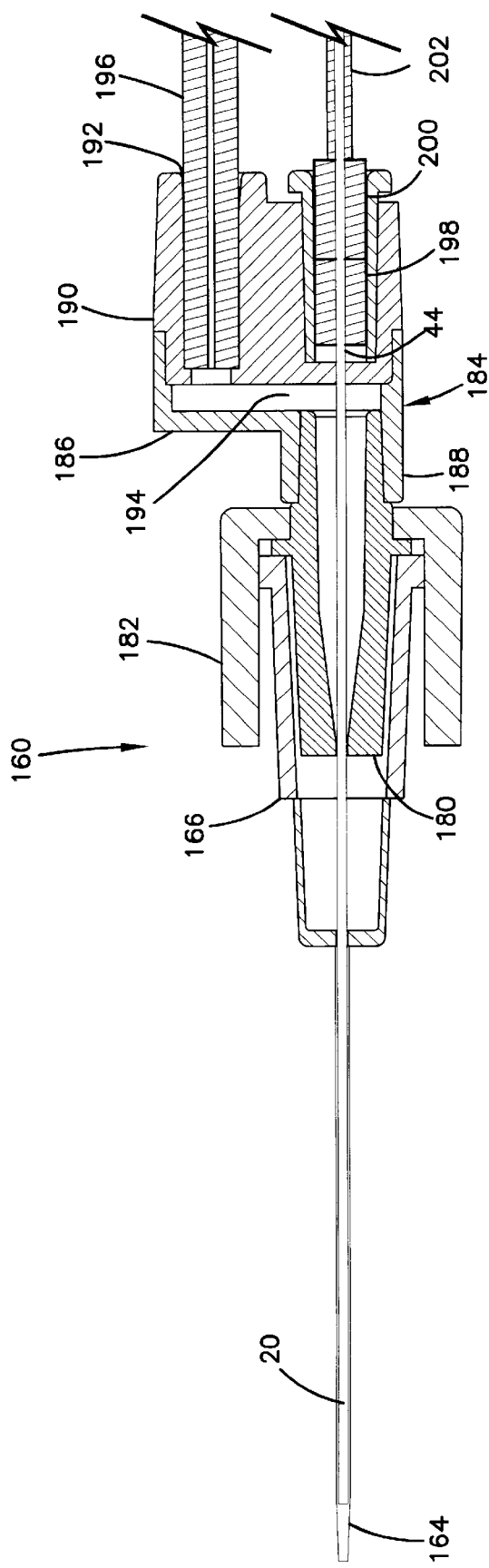
FIG. 8 is a longitudinal cross-section view of the assembled sensor assembly of FIG. 7.

FIGS. 7 and 8 illustrate an alternative sensor assembly 160 constructed in accordance with the principles of the present invention. The sensor assembly 160 includes an adapter 168 that connects to a luer fitting 166 of a catheter sheath 164. The adapter 168 includes an insertion piece 180 that fits within the luer fitting 166, and a cap 182 that threads on the luer fitting 166 to hold the insertion piece 180 within the luer fitting 166. The adapter 168 also includes a two-piece manifold 184. The manifold 184 includes a first piece 186 having a projection 188 that extends through the cap 182 and provides a fluid-tight connection with the insertion piece 180. The manifold 182 also includes a second piece 190 that connects with the first piece 186. The second piece 190 includes a tube receiver 192. The first and second pieces 186 and 190 of the manifold 184 cooperate to defined a flow passageway 194 (shown in FIG. 8) that extends from the tube receiver 192 to the insertion portion 180 of the adapter 168. In use, the tube receiver 192 preferably receives a tube 196 coupled to a source of calibration fluid (e.g., a syringe containing calibration fluid such as the syringe 71 of FIGS. 6A–6C).

Still referring to FIGS. 7 and 8, the sensor 20 preferably extends through the adapter 168 and into the catheter sheath 164. A first electrical connector 198 is mounted at the proximal end 44 of the sensor 20. The first electrical connector 198 is electrically coupled to a second electrical connector 200 that is mounted at the end of a wire 202. Preferably, the wire 202 is electrically coupled a controller such as the controller 42 of FIG. 4.

It is noted that the sensor assembly 160 does not include an internal reference electrode. Instead, the sensor assembly 160 can include an external reference electrode (e.g., a skin-mounted electrode) that is coupled to the controller.

Figure 9:
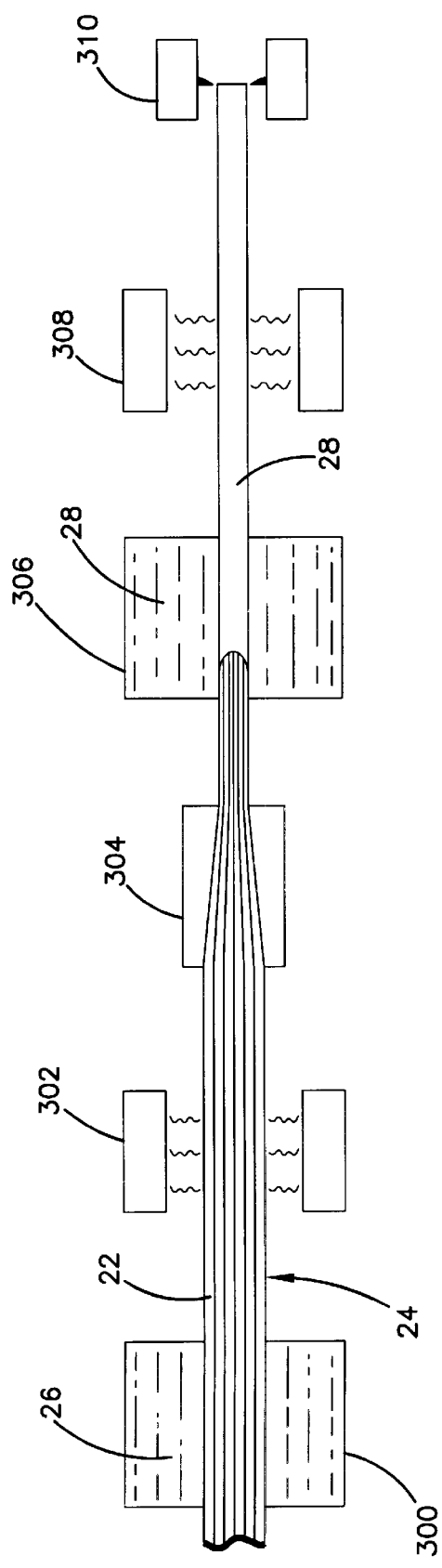
FIG. 9 is a schematic illustration of a method for manufacturing a sensor such as the sensor of FIG. 1.

FIG. 9 illustrates a method for making the sensor 20 of FIGS. 1–3. In practicing the method, the bundle 24 of fibers 22 is first pulled through a die 300 containing a volume of the sensing material 26 in liquid form. As the bundle 24 is pulled through the die 300, the sensing material 26 coats the outer surfaces of the fibers 22.

After the sensing material 26 has been applied to the fibers 22, the sensing material 26 can be dried at a heating station 302 (e.g., a convection heater). Thereafter, the fibers 22 coated with sensing material 26 are pulled through a sizing die 304 to compress the bundle 24 to a desired diameter. Next, the sized bundle 24 is pulled through a die 306 containing material that will form the insulating layer 28 of the sensor 20. For example, the die 306 can contain a volume of liquid polymer such as polyurethane. As the bundle 24 is pulled through the die 306, the insulating layer material coats the outside of the bundle. After the insulating layer 28 has been coated around the exterior of the bundle 24, the bundle can be moved through a curing station 308 (e.g., an ultraviolet curing station) where the insulating layer 28 is cured. Finally, the bundle 24 is moved through a cutting station 310 where the bundle 24 is cut into pieces having desired lengths.

The above-described method provides numerous advantageous. For example, the method allows a relatively large number of sensors 20 to be manufactured in a relatively short amount of time. Also, the above-described method is able to provide sensors having similar operating characteristics from batch to batch.

With regard to the foregoing description, it is to be understood that changes may be made in detail, especially in matters of the construction materials employed and the shape, size and arrangement of the parts without departing from the scope of the present invention. It is intended that the specification and depicted aspects be considered exemplary only, with a true scope and spirit of the invention being indicated by the broad meaning of the following claim.

What is claimed is:

1. A sensor comprising:
    a bundle of electrically conductive fibers having a desired bundle diameter;
    voids between the fibers for allowing analyte to diffuse into the sensor;
    a dry sensing material that is reactive with the analyte, the dry sensing material coating at least some of the fibers in the bundle; and
    an insulating layer surrounding the bundle of electrically conductive fibers.

2. The sensor of claim 1, wherein the insulating layer forms an analyte barrier that surrounds the bundle of conductive fibers.

3. The sensor of claim 2, wherein the analyte barrier defines at least one opening for allowing an analyte to access the sensing material.

4. The sensor of claim 1, wherein the insulating layer comprises an electrical insulator.

5. The sensor of claim 1, wherein the insulating layer comprises polyurethane.

6. The sensor of claim 1, wherein the conductive fibers comprise carbon.

7. The sensor of claim 1, wherein the sensing material includes a redox compound.

8. The sensor of claim 7, wherein the redox compound comprises a transition metal complex with one or more organic ligands.

9. The sensor of claim 7, wherein the sensing material includes a redox enzyme.

10. The sensor of claim 9, wherein the redox enzyme catalyzes the oxidation or reduction of an analyte.

11. The sensor of claim 10, wherein the analyte comprises lactate.

12. The sensor of claim 11, wherein the redox enzyme is selected from the group of lactate oxidize and lactate dehydrogenase.

13. The sensor of claim 10, wherein the analyte comprises glucose.

14. The sensor of claim 13, wherein the redox enzyme is selected from the group of glucose oxidize and glucose dehydrogenase.

15. The sensor according to claim 1, wherein the sensing material comprises a redox compound comprising an osmium transition metal complex with one or more organic ligands.

* * * * *

UNITED STATES PATENT AND TRADEMARK OFFICE
CERTIFICATE OF CORRECTION

PATENT NO. : 6,464,849 B1
DATED : October 15, 2002
INVENTOR(S) : Say et al.

It is certified that error appears in the above-identified patent and that said Letters Patent is hereby corrected as shown below:

Column 3,
Line 24, "glucose oxidize" should read -- glucose oxidase --
Line 25, "lactate oxidize" should read -- lactate oxidase --
Line 28, "Pelectrolysis" should read -- electrolysis --

Column 8,
Line 32, "lactate oxidize" should read -- lactate oxidase --
Line 37, "glucose oxidize" should read -- glucose oxidase --

Signed and Sealed this

First Day of July, 2003

JAMES E. ROGAN
*Director of the United States Patent and Trademark Office*